United States Patent

Kawabata et al.

[11] Patent Number: 5,958,914
[45] Date of Patent: Sep. 28, 1999

[54] CEPHEM COMPOUNDS

[75] Inventors: Kohji Kawabata, Kawanishi; Hirofumi Yamamoto; Yoshiteru Eikyu, both of Ikeda; Shinya Okuda, Kawanishi; Hisashi Takasugi, Sakai, all of Japan

[73] Assignee: Fujisawa Pharmaceutical Co., Ltd., Osaka, Japan

[21] Appl. No.: 09/043,578
[22] PCT Filed: Sep. 27, 1996
[86] PCT No.: PCT/JP96/02797
  § 371 Date: Mar. 26, 1998
  § 102(e) Date: Mar. 26, 1998
[87] PCT Pub. No.: WO97/12890
  PCT Pub. Date: Apr. 10, 1997

[30] Foreign Application Priority Data

Sep. 29, 1995 [GB] United Kingdom .................. 9519883

[51] Int. Cl.⁶ ...................... A61K 31/545; C07D 501/59; C07D 501/22; C07D 501/56
[52] U.S. Cl. .................. 514/206; 544/222; 544/225; 544/227
[58] Field of Search ................... 514/202, 203, 514/206; 544/222, 225, 227

[56] References Cited

U.S. PATENT DOCUMENTS 4,452,851  6/1984  Takaya ........................ 544/22

FOREIGN PATENT DOCUMENTS

| 55465 | 7/1982 | European Pat. Off. . |
| 2436787 | 9/1979 | France . |
| 3339667 | 5/1984 | Germany . |
| 8-151386 | 6/1998 | Japan . |
| 2034692 | 6/1980 | United Kingdom . |

OTHER PUBLICATIONS

Mochida, Chem Abs 110, 114556, May 1986.

*Primary Examiner*—Mark L. Berch
*Attorney, Agent, or Firm*—Oblon, Spivak, McClelland, Maier & Neustadt, P.C.

[57] ABSTRACT

A compound of the formula:

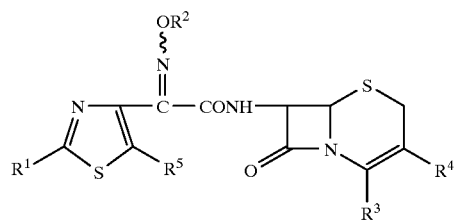

wherein $R^1$ is amino, $R^2$ is hydrogen, $R^3$ is carboxy, $R^4$ is heterocyclic(lower)alkylthio wherein said heterocyclic group is pyrazolyl and said lower alkyl group is methyl, and $R^5$ is halogen; and pharmaceutically acceptable salts thereof.

5 Claims, No Drawings

CEPHEM COMPOUNDS

This application is a 371 of PCT/JP96/02797, filed Sep. 27, 1996.

TECHNICAL FIELD

The present invention relates to new cephem compounds and pharmaceutically acceptable salts thereof.

More particularly, it relates to new cephem compounds and pharmaceutically acceptable salts thereof, which have antimicrobial activities, to processes for preparation thereof, to pharmaceutical composition comprising the same and to a method for treating infectious diseases in human being and animals.

Accordingly, one object of the present invention is to provide the cephem compounds and pharmaceutically acceptable salts thereof, which show highly activity against a number of pathogenic microorganisms.

Another object of the present invention is to provide processes for the preparation of the cephem compounds and salts thereof.

A further object of the present invention is to provide a pharmaceutical composition comprising, as an active ingredient, said cephem compounds or their pharmaceutically acceptable salts.

Still further object of the present invention is to provide a method for treating infectious diseases caused by pathogenic microorganisms, which comprises administering said cephem compounds to infected human being or animals.

DISCLOSURE OF INVENTION

The object cephem compounds of the present invention are novel and can be represented by the following general formula (I):

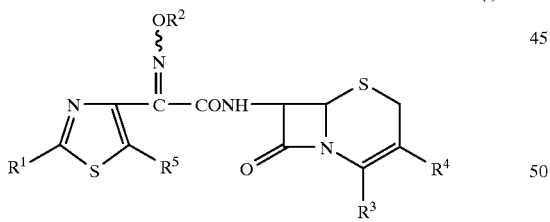

(I)

wherein $R^1$ is amino or protected amino, $R^2$ is hydrogen or hydroxy protective group, $R^3$ is carboxy or protected carboxy, $R^4$ is hydrogen, lower alkenyl, acyloxy(lower)alkenyl, optionally substituted heterocyclic(lower)alkenyl, optionally substituted heterocyclic(lower)alkenylthio, optionally substituted heterocyclic(lower)alkylthio or optionally substituted heterocyclic-thio(lower)alkylthio, and R5 is halogen or lower alkyl The object compound (I) of the present invention can be prepared by the following processes.

Process (1)

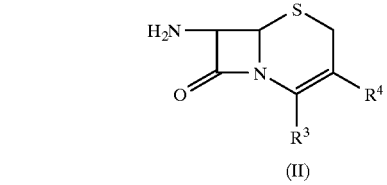

(II)

or its reactive derivative at the amino group, or a salt thereof

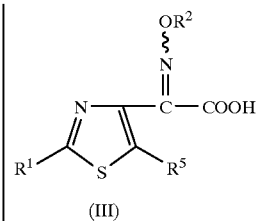

(III)

or its reactive derivative at the carboxy group, or a salt thereof

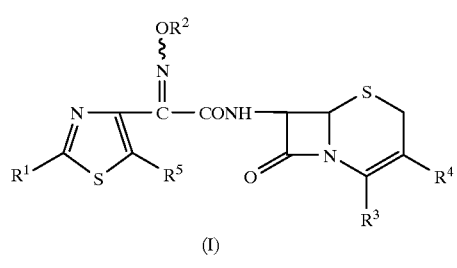

(I)

or a salt thereof

Process (2)

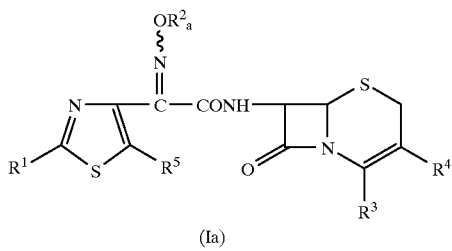

(Ia)

or a salt thereof elimination reaction of the hydroxy protective group

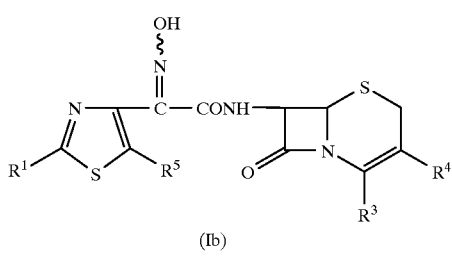

(Ib)

or a salt thereof

Process (3)

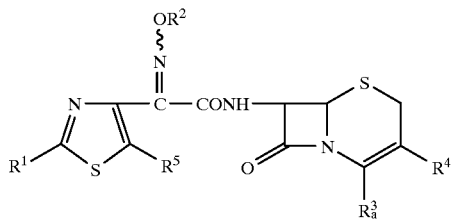

(Ic)

or a salt thereof

↓ elimination reaction of
the carboxy protective group

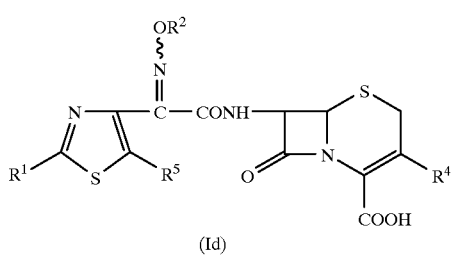

(Id)

or a salt thereof

Process (4)

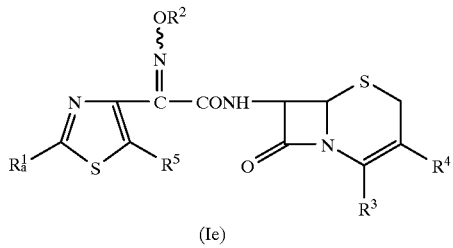

(Ie)

or a salt thereof

↓ elimination reaction of
the amino protective group

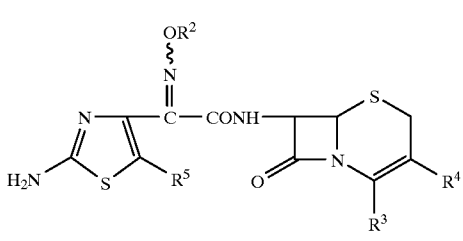

(If)

or a salt thereof

Process (5)

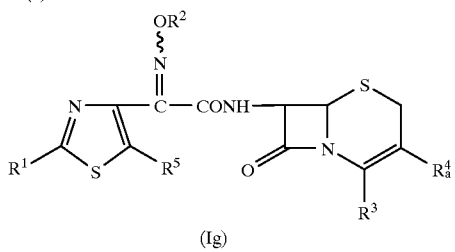

(Ig)

or a salt thereof

↓ elimination reaction of
the imino protective group

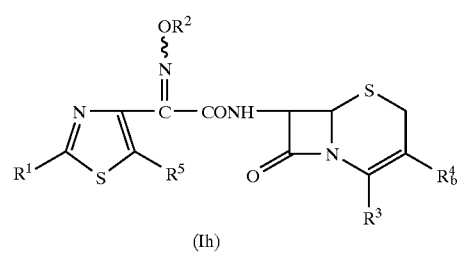

(Ih)

or a salt thereof wherein $R^1$, $R^2$, $R^3$, $R^4$ and $R^5$ are each as defined above, $R_a^1$ is protected amino, $R_a^2$ is hydroxy protective group, $R_a^3$ is protected carboxy and $R_a^4$ is heterocyclic(lower)alkylthio which is substituted by an imino protective group and $R_b^4$ is heterocyclic(lower)alkylthio.

Regarding the compounds (I), (Ia), (Ib), (Ic), (Id), (Ie), (If), (Ig), (Ih) and (III), it is to be understood that said compounds include syn isomer(Z), anti isomer (E) and a mixture thereof.

For example, with regard to the object compound (I), syn isomer(Z) means one geometrical isomer having the partial structure represented by the following formula:

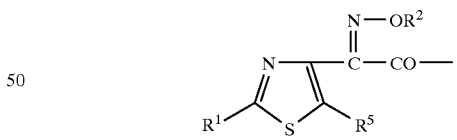

(wherein $R^1$, $R^2$ and $R^5$ are each as defined above), and anti isomer(E) means the other geometrical isomer having the partial structure represented by the following formula

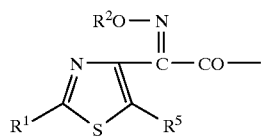

(wherein $R^1$, $R^2$ and $R^5$ are each as defined above), and all of such geometrical isomers and mixture thereof are included within the scope of this invention.

In the present specification and claims, the partial structure of these geometrical isomers and mixture thereof are represented for convenient sake by the following formula:

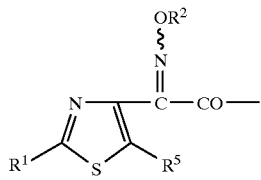

(wherein $R^1$, $R^2$ and $R^5$ are each as defined above).

It is to be noted that the compound (I) and the other compounds of this invention may include one or more stereoisomers due to asymmetric carbon atom(s), and all of such isomers and mixture thereof are included within the scope of this invention.

In the above and subsequent descriptions of the present specification, suitable examples and illustrations of the various definitions, which the present invention include within the scope thereof, are explained in detail as follows.

The term "lower" is intended to mean 1 to 6 carbon atom(s) unless otherwise indicated.

Suitable "lower alkyl" may include straight or branched one such as methyl, ethyl, propyl, isopropyl, butyl, t-butyl, pentyl, hexyl, and the like, in which more preferred one may be $C_1$–$C_4$ alkyl and the most preferred one may be methyl, ethyl or propyl.

Suitable "lower alkenyl" may be straight or branched ones such as vinyl, allyl, 2-butenyl, 2-methyl-3-butenyl, 3-pentenyl, 1-hexenyl, or the like, in which the preferred one may be ($C_2$–$C_4$)alkenyl.

Suitable "aryl" may include phenyl, naphthyl and the like.

Suitable "protected amino" may include an acylamino or an amino group substituted by a conventional protecting group such as ar (lower) alkyl which may have suitable substituent(s) (e.g. benzyl, trityl, etc.) or the like.

Suitable "acyl moiety" in the term "acylamino" and "acyloxy" may include optionally substituted carbamoyl, aliphatic acyl group and acyl group containing an aromatic or heterocyclic ring. And suitable examples of the said acyl maybe lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.); arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc.); ar(lower)alkoxycarbonyl (e.g. benzyloxycarbonyl, phenethyloxycarbonyl, etc.); carbamoyl; N-(lower)alkylcarbamoyl (e.g. N-methylcarbamoyl, N-ethylcarbamoyl, N-isopropylcarbamoyl, N-butylcarbamoyl, etc.); N,N-di(lower)alkylcarbamoyl (e.g. N,N-dimethylcarbamoyl, N,N-diethylcarbamoyl, N-metyl-N-ethylcarbamoyl, N,N-diisopropylcarbamoyl, N,N-dibutylcarbamoyl, etc.), and the like. The acyl moiety as stated above may have suitable substituent(s) such as halogen (e.g. chlorine, bromine, iodine or fluorine), lower alkyl as defined above, or the like.

Suitable "protected carboxy" may include esterified carboxy and the like. And suitable example of said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, etc.); lower alkenyl ester (e.g., vinyl ester, allyl ester, etc.); lower alkynyl ester (e.g., ethynyl ester, propynyl ester, etc.); lower alkoxyalkyl ester (e.g., methoxymethyl ester, ethoxymethyl ester, isopropoxymethyl ester, 1-methoxyethyl ester, 1-ethoxyethyl ester, etc.); lower alkylthioalkyl ester (e.g., methylthiomethyl ester, ethylthiomethyl ester, ethylthioethyl ester, isopropylthiomethyl ester, etc.); mono(or di or tri)halo (lower)alkyl ester (e.g. 2-iodoethyl ester, 2,2,2-trichloroethyl ester, etc.); lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 1-acetoxyethyl ester, 2-acetoxyethyl ester, 1-propionyloxyethyl ester, etc.); cyclo(lower)alkylcarbonyloxy(lower)alkyl ester (e.g., 1-(cyclohexylcarbonyloxy)ethyl ester, etc.); lower alkoxycarbonyloxy(lower)alkyl ester (e.g., methoxycarbonyloxymethyl ester, ethoxycarbonyloxymethyl ester, propoxycarbonyloxymethyl ester, 1-(or 2-)-[methoxycarbonyloxy]ethyl ester, 1-(or 2-) [ethoxycarbonyloxy]ethyl ester, 1-(or 2-) [propoxycarbonyloxy]ethyl ester, 1-(or 2-) [isopropoxycarbonyloxy]ethyl ester, etc.); cyclo(lower) alkyloxycarbonyloxy(lower)alkyl ester (e.g., 1-(cyclohexyloxycarbonyloxy)ethyl ester, etc.); lower alkanesulfonyl(lower)alkyl ester (e.g. mesylmethyl ester, 2-mesylethyl ester etc.); ar(lower)alkyl ester, for example, phenyl (lower) alkyl ester which may have one or more suitable substituent(s) (e.g., benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3, 5-di-t-butylbenzyl ester, etc.); aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester; lower alkylthioester (e.g. methylthioester, ethylthioester, etc.) and the like.

Suitable "hydroxy protective group" may include an acyl group which is examplified in definition of "acyl moiety", cyclo(lower)alkenyl (preferable example is cyclo(C3-8) alkenyl such as cyclopentenyl or cyclohexenyl, etc.) ar(lower)alkyl which may have one or more suitable substituent(s) (e.g., benzyl, 4-methoxybenzyl, trityl, etc.), trisubstituted silyl (e.g., trimethylsilyl, t-butyldimethylsilyl, etc.), tetrahydropyranyl and the like.

Suitable "heterocyclic group" in the "optionally substituted heterocyclic(lower)alkenyl", "optionally substituted heterocyclic(lower)alkenylthio", "optionally substituted heterocyclic(lower)alkylthio" and "optionally substituted heterocyclic-thio (lower) alkylthio" means saturated or unsaturated, monocyclic or polycyclic heterocyclic group containing at least one hetero-atom such as an oxygen, sulfur, nitrogen atom and the like. And, especially preferably heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.; saturated 3 to 8-membered heteromonocyclic group containing 1 to 4 nitrogen atom(s), for example, pyrrolidinyl, imidazolidinyl, piperidyl (e.g. piperidino, etc.), piperazinyl, etc.; unsaturated condensed heterocyclic group containing 1 to 5 nitrogen atom(s), for example, indolyl, isoindolyl, indolizynyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.; unsaturated 3 to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.; saturated 3 to 8-membered heteromonocyclic group containing 1 to 2 oxygen atom(s) and 1 to 3 nitrogen atom(s), for example, morpholinyl, oxazolidinyl (e.g. 1,3-oxazolidinyl, etc.), etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered heteromonocyclic group containing 1 to 2 sulfur atom(s) and 1 to 3 nitrogen atom(s), for example, 1,3-thiazolyl, 1,2-thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.; saturated 3 to 8-membered heteromonocyclic group containing 1 to 2 sulfur atom(s) and 1 to 3 nitrogen atom(s), for example thiazolidinyl, etc.; unsaturated 3 to 8-membered heteromonocyclic group containing a sulfur atom, for example, thienyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered heteromonocyclic group containing 1 to 2 oxygen atom(s), for example, furyl, pyranyl, dioxolyl, etc.; saturated 3 to 8-membered heteromonocyclic group containing 1 to 2 oxygen atom(s), for example, oxolanyl, tetrahydropyranyl (e.g. tetrahydro-2H-pyran-2-yl, etc.), dioxolanyl, etc.; unsaturated condensed heterocyclic group containing 1 to 2 oxygenatom(s), forexample, isobenzofuranyl, chromenyl (e.g. 2H-chromen-3-yl, etc.), dihydrochromenyl (e.g. 3,4-dihydro-2H-chromen-4-yl, etc.), etc.; and the like.

Most preferable "heterocyclic group" in the "optionally substituted heterocyclic(lower)alkenyl", "optionally substituted heterocyclic(lower)alkenylthio", "optionally substituted heterocyclic(lower)alkylthio" and "optionally substituted heterocyclic-thio-(lower)alkylthio" may be unsaturated 3 to 8-membered heteromonocyclic group containing 1 to 3 nitrogen atom(s), for example, pyrazolyl, pyridyl and triazolyl (e.g., 4H-1,2,4-triazolyl, 1H-1,2,3-triazolyl 2H-1,2,3-triazolyl, etc.).

This "heterocyclic group" may have one or more (preferably 1 to 4) suitable substituent(s) such as lower alkyl, hydroxy, cyano, imino protective group or the like, in which the preferred one may be imino protective group.

Suitable "imino protective group" may include a conventional amino protective group such as ar(lower)alkyl which may have suitable substituent(s) as exemplified before, an acyl group which is exemplified in the definition of "acylamino" as exemplified and the like.

Suitable "halogen" may include fluoro, chloro, bromo and iodo.

Suitable pharmaceutically acceptable salts of the object compound (I) are conventional non-toxic salts and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. formate, acetate trifluoroacetate, maleate, tartrate, methanesulfonate, benzenesulfonate, toluenesulfonate, etc.), an inorganic acid salt (e.g. hydrochloride, hydrobromide, sulfate, phosphate, etc.), a salt with an amino acid (e.g. arginine salt, aspartic acid salt, glutamic acid salt, etc.), and the like.

The processes for preparing the object of the present invention are explained in detail in the following.

Process (1)

The compound (I) or a salt thereof can be prepared by reacting the compound (II) or its reactive derivative at the amino group, or a salt thereof with the compound (III) or its reactive derivative at the carboxy group, or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsilyl) acetamide [e.g. N-(trimethylsilyl)-acetamide], bis (trimethylsilyl)urea or the like; a derivative formed by the reaction of the compound (II) with phosphorus trichloride or phosgene and the like.

Suitable reactive derivative at the carboxy group of the compound (III) may include an acid halide, an acid anhydride, an activated amide, an activated ester, and the like. Suitable examples of the reactive derivative may be an acid chloride; an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.), aliphatic carboxylic acid (e.g. acetic acid, propionic acid, butyric acid, isobutyric acid, pivalic acid, pentanoic acid, isopentanoic acid, 2-ethylbutyric acid, trichloroacetic acid, etc.) oraromatic carboxylic acid (e.g. benzoic acid, etc.); a symmetrical acid anhydride; an activated amide with imidazole, 4-substituted imidazole, 1-hydroxy-1H-benzotriazole, dimethylpyrazole, triazole or tetrazole; or an activated ester (e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-1H-benzotriazole, etc.), and the like. These reactive derivatives can optionally be selected from the above according to the kind of the compound (III) to be used.

The reaction is usually carried out in a conventional solvent such as acetonitrile, chloroform, methylene chloride, ethylene chloride, tetrahydrofuran, ethyl acetate, N,N-dimethylformamide, pyridine, water, alcohol (e.g. methanol, ethanol, etc.), acetone, dioxane, or any other organic solvent which does not adversely influence the reaction. These conventional solvent may also be used in a mixture.

In this reaction, when the compound (III) is used in a free acid form or its salt form, the reaction is preferably carried out in the presence of a conventional condensing agent such as N,N'-dicyclohexylcarbodiimide; N-cyclohexyl-N'- morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonyl-bis(2-methylimidazole); pentamethylene-ketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate (e.g. ethyl chloroformate, isopropyl chloroformate, etc.); triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine (e.g. triethylamine, diisopropylethylamine, etc.), pyridine, N-(lower) alkylmorpholine, N,N-di(lower)alkylbenzylamine, or the like.

The reaction temperature is not critical, and the reaction is usually carried out under cooling to warming.

Process (2)

The compound (Ib) or a salt thereof can be prepared by subjecting the compound (Ia) or a salt thereof to an elimination reaction of the hydroxy protective group. Suitable method of this elimination reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an metal hydroxide (e.g. sodium hydroxide, magnesium hydroxide, etc.), metal alkoxide (e.g. sodium methoxide, potassium methoxide, etc.), metal carbonate or metal bicarbonate, trialkylamine (e.g. trimethylamine, triethylamine, etc.), picoline, 1,5-diazabicyclo[4.3.0]-non-5-ene, 1,4-diazabicyclo[2.2.2] octane, 1,8-diazabicyclo[5.4.0]undec-7-ene, or the like.

Suitable acid may include an organic acid (e.g. formic acid, acetic acid, propionic acid, trichloroacetic acid, trifluoroacetic acid, etc.) and an inorganic acid (e.g. hydrochloric acid, hydrobromic acid, sulfuric acid, hydrogen chloride, hydrogen bromide, ammonium chloride, etc.). The elimination reaction using Lewis acid such as trihaloacetic acid (e.g. trichloroacetic acid, trifluoroacetic acid, etc.) or the like is preferably carried out in the presence of cation trapping agents (e.g. anisole, phenol, etc.).

The reaction is usually carried out in a solvent such as water, an alcohol (e.g. methanol, ethanol, etc.), methylene chloride, tetrahydrofuran, a mixture thereof or any other solvent which does not adversely influence to the reaction. A liquid base or acid can be also used as the solvent. The reaction temperature is not critical and the reaction is usually carried out under cooling to warming.

(ii) For Reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, dioxane, tetrahydrofuran, N,N-dimethylformamide, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

The present invention includes, within the scope of the invention, the case that the protected amino group in $R^1$ and/or the protected carboxy group in $R^3$ and/or the imino protective group in $R^4$ are/is transformed into an amino group and/or a carboxy group and/or a hydrogen during this reaction respectively.

Process (3)

The compound (Id) or a salt thereof can be prepared by subjecting the compound (Ic) or a salt thereof to an elimination reaction of the carboxy protective group.

This reaction can be carried out in a similar manner to that of the aforementioned Process (2), and therefore the reagents to be used and the reaction conditions (e.g., solvent, reaction temperature, etc.) can be referred to those of the Process (2).

The present invention includes, within the scope of the invention, the case that the protected amino group in $R^1$ and/or the hydroxy protective group in $R^2$ and/or the imino protective group in $R^4$ are/is transformed into an amino group and/or a hydrogen and/or a hydrogen during this reaction respectively.

Process (4)

The compound (If) or a salt thereof can be prepared by subjecting the compound (Ie) or a salt thereof to an elimination reaction of the carboxy protective group.

This reaction can be carried out in a similar manner to that of the aforementioned Process (2), and therefore the reagents to be used and the reaction conditions (e.g., solvent, reaction temperature, etc.) can be referred to those of the Process (2).

The present invention includes, within the scope of the invention, the case that the hydroxy protective group in $R^2$ and/or the protected carboxy group in $R^3$ and/or the imino protective group in $R^4$ are/is transformed into a hydrogen and/or an carboxy group and/or a hydrogen during this reaction respectively.

Process (5)

The compound (Ih) or a salt thereof can be prepared by subjecting the compound (Ig) or a salt thereof to an elimination reaction of the carboxy protective group.

This reaction can be carried out in a similar manner to that of the aforementioned Process (2), and therefore the reagents to be used and the reaction conditions (e.g., solvent, reaction temperature, etc.) can be referred to those of the Process (2).

The present invention includes, within the scope of the invention, the case that the protected amino group in $R^1$ and/or the hydroxy protective group in R² and/or the protected carboxy group in R³ are/is transformed into an amino group and/or a hydrogen and/or a hydrogen during this reaction respectively.

Suitable salts of the object and starting compounds and their reactive derivatives in Processes (1)–(5) can be referred to the ones as exemplified for the compound (I).

The object compound (I) and pharmaceutically acceptable salts thereof are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound (I), the test data on MIC (minimal inhibitory concentration), urinary excretion, bile excretion and blood concentration of representative compound of this invention are shown in the following.

(A) Minimal Inhibitory Concentration

Test Method:

In vitro antibacterial activity were determined by the two-fold agar-plate dilution method as described below.

One loopful of an overnight culture of each test strain in Trypticase-soy broth ($10^8$ viable cells per ml) was streaked on heart infusion agar (HI-agar)containing graded concentrations of representative test compound, and the minimal inhibitory concentration (MIC) was expressed in terms of mg/ml after incubation at 37° C. for 20 hours.

Test compound:
(1) 7β-[2-(2-Amino-5-chlorothiazol-4-yl)-2-(Z)-(hydroxyimino)-acetamido]-3-[(pyrazol-4-yl)methyl-thio]-3-cephem-4-carboxylic acid.
(2) 7β-[2-(2-Amino-5-chlorothiazol-4-yl)-2-(Z)-(hydroxyimino)-acetamido]-3-[(3-pyridyl)methyl-thio3-cephem-4-carboxylic acid.
(3) 7β-[2-(2-Amino-5-chlorothiazol-4-yl)-2-(Z)-(hydroxyimino)-acetamido]-3-[(1H-1,2,3-triazol-5-yl)methylthio]-3-cephem-4-carboxylic acid.

Test result:

MIC (mg/ml)

| Test strain | Test compound | | |
|---|---|---|---|
| | (1) | (2) | (3) |
| *E. faecalis* | 2.9 | 2.1 | 2.1 |
| Penicillin resistant *S. pneumoniae* | 0.72 | 0.49 | 0.36 |
| Methicillin susceptible *S. aureus* | 0.25 | 0.23 | 0.27 |

(B) Urinary Excretion

Test Method

Male JCL SD atrain rats (age, 6 weeks) were used. Test compound was suspended in 0.5% methyl cellurose solution. The rats were atarved overnight before dosing with 20 mg /kg. Urine samples were collected at 0 to 6 and 6 to 24 hours after oral administration. Bile samples were collected at same interval as that of urine samples after a polyethylene cannula was inserted into the bile duct. Plasma samples were obtained by heart puncture at specified times after dosing. Concentrations of test compounds were measured by the disc-plate diffusion method using *E. coli* ATCC 39188 as test organism and nutrient agar (Difco) as the test medium. The diluents for standard curves were prepared with plasma from rat for determining the plasma levels, with 1/15 M phosphate buffer (pH7.0) for determining the urinary and biliary levels. The plate were incubated at 37° C. for 18 hours and the zone of inhibition were measured and the recovery rate was calculated by comparing with the standard.

Test Compound
(1) 7β-[2-(2-Amino-5-chlorothiazol-4-yl)-2-(Z)-(hydroxyimino)acetamido]-3-[(pyrazol-4-yl)-methylthio]-3-cephem-4-carboxylic acid.
(2) 7β-[2-(2-Amino-5-chlorothiazol-4-yl)-2-(Z)-(hydroxyimino)-acetamido]-3-[(3-pyridyl)methyl-thio]-3-cephem-4-carboxylic acid.
(3) 7β-[2-(2-Amino-5-chlorothiazol-4-yl)-2-(Z)-(hydroxyimino)-acetamido]-3-[(1H-1,2,3-triazol-5-yl)methylthio]-3-cephem-4-carboxylic acid.

Test result

| | Test compound | | |
|---|---|---|---|
| | (1) | (2) | (3) |
| Urinary recovery in 24 hours (%) | 39.7 | 17.0 | 7.62 |
| Biliary recovery in 24 hours (%) | 29.0 | 19.6 | 37.5 |
| Plasma level: Cmax (μg/ml) | 21.8 | | |
| Plasma level: AUC (μg · h/ml) | 52.9 | | |

For therapeutic administration, the object compound (I) and pharmaceutically acceptable salts thereof of the present invention are used in a form of conventional pharmaceutical preparation which contains said compound as an active ingredient, in admixture with pharmaceutically acceptable carriers such as an organic or inorganic solid or liquid excipient which is suitable for oral, parenteral and external administration.

The pharmaceutical preparations may be in solid form such as tablet, granule, powder, capsule, or liquid form such as solution, suspension, syrup, emulsion, lemonade and the like.

In needed, there may be included in the above preparations, auxiliary substances, stabilizing agents, wetting agents and other commonly used additives such as lactose, citric acid, tartaric acid, stearic acid, magnesium stearate, terra alba, sucrose, corn starch, talc, gelatin, agar, pectin, peanut oil, olive oil, cacao butter, ethylene glycol, and the like.

While the dosage of the compound (I) may vary and depend upon the age, conditions of the patient, a kind of diseases, a kind of the compound (I) to be applied, etc. In general, amounts between 1 mg and about 4,000 mg or even more per day may be administered to a patient. An average single dose of about 10 mg, 50 mg, 100 mg, 250 mg, 500 mg, 1000 mg of the object compound (I) of the present invention may be used in treating diseases infected by pathogenic microorganisms.

The following Preparations and Examples are given for the purpose of illustrating the present invention in more detail.

Preparation 1

To acetic anhydride (20.6 ml) was added formic acid (16.6 ml) at 15° C. The mixture was stirred at room temperature for 30 minutes. To the mixture was 2-(2-aminothiazol-4-yl)-2-(Z)-(acetoxyimino)acetic acid (10 g) under ice-cooling, and the reaction mixture was stirred at room temperature for 20 hours. To the mixture was added isopropyl ether (37.2 ml) under ice-cooling, and the mixture was stirred at the same temperature for 1 hour. The resulting precipitate was collected by filtration to give 2-(2-formylaminothiazol-4-yl)-2-(Z)-(acetoxyimino)acetic acid (9.39 g).

IR (KBr): 1768, 1747, 1652 cm$^{-1}$; NMR (DMSO-d$_6$, δ): 2.20 (3H, s), 7.89 (1H, s), 8.56 (1H, s), 12.72 (1H, s)

Preparation 2

To a suspension of 2-(2-formylaminothiazol-4-yl)-2-(Z)-(acetoxyimino)acetic acid (5 g) in tetrahydrofuran (50 ml) was added N-chlorosuccinimide (3.89 g) at room temperature. After the mixture was stirred at room temperature for 5 hours 28 minutes, the reaction mixture was poured into a mixture of 5% aqueous sodium thiosulfate solution (25 ml) and ethyl acetate (50 ml) under ice-cooling. The mixture was adjusted to pH 3.0 with 30% aqueous potassium carbonate solution under ice-cooling, stirred for 1 hour at the same temperature, and the resulting precipitate was collected by filtration to give 2-(5-chloro-2-formylaminothiazol-4-yl)-2-(Z)-(acetoxyimino)-acetic acid (4.02 g).

IR (KBr): 1770, 1691, 1623 cm$^{-1}$; NMR (DMSO-d$_6$, δ): 1.91 (3H, s), 8.41 (1H, s)

Preparation 3

Under nitrogen atmosphere, 2-(5-chloro-2-formaminothiazol-4-yl)-2-(Z)-(acetoxyimino)acetic acid (43.8 g) was added to a suspension of phosphorous pentachloride (37.5 g) in dichloromethane (300 ml) under −15° C. Stirring was continued for 2.5 hours, the mixture was diluted with heptane (900 ml), and stirred for 30 minutes at 0° C. The resulting precipitate was collected by filtration to afford 2-(5-chloro-2-formaminothiazol-4-yl)-2-(Z)-(acetoxyimino)acetyl chloride (65.1 g) as a crude powder containing residual heptane.

IR (KBr): 1799.3, 1691.3 cm$^{-1}$; NMR (DMSO-d$_6$, δ): 2.24 (3H, s), 8.54 (1H, s)

Preparation 4

(2-Amino-5-bromothiazol-4-yl)-2-(Z)-(acetoxyimino)-acetic acid (3.84 g) was obtained from N-bromosuccinimide (10.65 g) and 2-(2-aminothiazol-4-yl)-2-(Z)-(acetoxyimino)-acetic acid (6.87 g) according to a similar manner to that of Preparation 2.

IR (KBr): 3479.0, 3122.2, 1760.7, 1639.2 cm$^{-1}$ NMR (DMSO-d$_6$, δ): 2.20 (3H, s), 7.58 (2H, s), 7.79 (1H, s)

Preparation 5

A mixture of ethyl chlorofluoroacetate (100 g), phthaloyl chloride (102.5 ml) and chlorosulfonic acid (47.3 ml) was heated at total reflux in a still connected to an ice-cooled receiver backed up by a dry ice cooled trap. When the pot temperature reached 120° C., distillation was started and the volatile material was distilled from the reaction mixture until the pot temperature rose to 200° C. The condensates in the receiver and the dry ice cooled trap were combined.

On the other hand, isopropylidene malonate (51.3 g) was dissolved in a solution of pyridine (69.7 ml) in dichloromethane (160 ml). To the solution was added dropwise above obtained combined solution at 5° C. to 10° C. and the mixture was stirred for 3 hours at the same temperature. The solution was poured into a cooled 3N hydrochloric acid (200 ml). The separated organic phase was washed with brine (200 ml), and dried with magnesium sulfate and evaporated in vacuo. The residue was added methanol (300 ml) at room temperature with stirring. The mixture was refluxed for 8 hours. The reaction mixture was evaporated in vacuo. The residue was subjected to a column chromatogaphy on silica gel (500 g) and eluted with a mixture of ethyl acetate and hexane (1:2). The fractions containing the object compound were collected, evaporated to give methyl 4-chloro-4-fluoro-3-oxobutyrate (43.2 g).

NMR (DMSO-d$_6$, δ): 3.72 (3H, s), 3.88 (2H, d, J=1.6 Hz), 6.99 (1H, d, J=49 Hz)

Preparation 6

To a solution of methyl 4-chloro-4-fluoro-3-oxobutyrate (31 g) andisopentylnitrite (25.8 ml) indichloromethane (120 ml) was added dropwise acetylchloride (13 ml) under ice-cooling with stirring and the mixture was stirred for 3 hours at 50° C. to 100° C. The resulting solution was poured into water (300 ml) and adjusted to pH 3.0 with saturated aqueous sodium bicarbonate. The separated organic phase was washed with water (300 ml) and dried with magnesium sulfate and evaporated in vacuo to give methyl 4-chloro-4-fluoro-2-(hydroxyimino)-3-oxobutyrate.

NMR (DMSO-d$_6$, δ): 3.82 (3H, s), 7.39 (1H, d, J=49 Hz), 14.14 (1H, s)

Preparation 7

To a solution of methyl 4-chloro-4-fluoro-2-(hydroxyimino)-3-oxobutyrate (7.8 g) in N,N-dimethylacetamide (80 ml) was added thiourea (15 g) under stirring at 300° C. and then the stirring was continued for 12 hours at the same temperature. The resulting solution was powered into a mixture of ethyl acetate (300 ml) and water (400 ml), and adjusted to pH 3.0 with saturated aqueous sodium hydrogencarbonate. The separated organic phase was washed with water (400 ml), and brine (400 ml), and dried with magnesium sulfate and evaporated in vacuo to give methyl 2-(2-amino-5-fluorothiazol-4-yl)-2-(Z)-(hydroxyimino)acetate (2.17 g).

NMR (DMSO-d$_6$, δ): 3.76 (3H, s), 7.11 (2H, br s), 11.92 (1H, s)

Preparation 8

To a suspension of methyl 2-(2-amino-5-fluorothiazol-4-yl)-2-(Z)-(hydroxyimino)acetate (1 g) in dichloromethane (20 ml) was added dropwise 1M borontrichloride solution in dichloromethane (22.8 ml) under ice-cooling with stirring, and the mixture was stirred for 3 hours at 50° C. to 10° C. The resulting solution was poured into a mixture of tetrahydrofuran (30 ml) and brine (15 ml), and adjusted to pH 3.0 with saturated aqueous sodium bicarbonate. The separated organic phase was dried with magnesium sulfate and evaporated in vacuo. The residue was subjected to a column chromatography on silica gel and eluted with a mixture of ethyl acetate and methanol (2:1). The fractions containing the object compound were combined and evaporated in vacuo to give 2-(2-amino-5-fluorothiazol-4-yl)-2-(Z)-(hydroxyimino)acetic acid (330.26 mg).

NMR (DMSO-d$_6$, δ): 6.94 (2H, br s); MASS: 206 (M$^+$)

Preparation 9

A mixture of acetic anhydride (2.7 ml) and formic acid (2.2 ml) was stirring for 30 minutes at 30° C. 2-(2-Amino-5-fluorothiazol-4-yl)-2-(Z)-(hydroxyimino) acetic acid (1.2 g) was added thereto with stirring under ice cooling, and the mixture was stirred for 3 hours at 25 to 35° C. The reaction mixture was poured into an isopropyl ether (50 ml). The resulting precipitate was collected by filtration, dried under reduced pressure to give 2-(5-fluoro-2-formylaminothiazol-4-yl)-2-(Z)-(formyloxyimino)acetic acid (0.65 g).

NMR (DMSO-d$_6$, δ): 8.23 (1H, s), 8.50 (1H, s)

Preparation 10

A solution of ethyl 3-oxopentanoate (50 g) in acetic acid (66 ml) was cooled to 0° C. and treated dropwise with 2/3 portion of a solution of sodium nitrite (52.6 g) in water (170 ml). After dropping (40 minutes), the reaction mixture was diluted with water (170 ml) and stirred for 1.5 hours. The mixture was treated with the residual solution of sodium nitrite at room temperature and stirred for more 1.5 hours. The reaction mixture was diluted with ether and quenched by aqueous sodium bicarbonate. The organic phase was washed with brine and dried with magnesium sulfate. The solvent was removed under reduced pressure to afford ethyl 2-(Z)-hydroxyimino-3-oxopentanoate (43.77 g).

IR (Neat): 3352, 1747, 1724, 1691 cm$^{-1}$; NMR (DMSO-d$_6$, δ): 13.17 (1H, s), 4.23 (2H, q, J=7.1 Hz), 2.79 (2H, q, J=7.3 Hz), 1.22 (3H, t, J=7.1 Hz), 0.99 (3H, t, J=7.3 Hz)

Preparation 11

A solution of ethyl 2-(Z)-hydroxyimino-3-oxopentanoate (10 g) in 10 ml of acetic acid was cooled to 0° C. and treated dropwise with sulfuryl chloride (5.3 ml). The mixture was stirred for 3 hours at room temperature and quenched by ice-water. The mixture was extracted with ethyl acetate, and the extracts were washed with brine and dried with magnesium sulfate. The solvent was removed under reduced pressure to afford ethyl 4-chloro-2-(Z)-hydroxyimino-3-oxopentanoate (11.97 g).

IR (Neat): 3371, 1736, 1703 cm$^{-1}$; NMR (DMSO-d$_6$, δ): 13.71 (1H, s), 5.34 (1H, q, J=6.7 Hz), 4.29 (2H, q, J=7.1 Hz), 1.58 (3H, d, J=6.7 Hz), 1.25 (3H, t, J=7.1 Hz)

Preparation 12

Ethyl 2-(2-amino-5-methylthiazol-4-yl)-2-(Z)-(hydroxyimino)acetate (2.75 g) was obtained from ethyl 4-chloro-2-(Z)-hydroxyimino-3-oxopentanoate (4 g) according to a similar manner to that of Preparation 7.

IR (Neat): 3163, 1724, 1618 cm$^{-1}$; NMR (DMSO-d$_6$, δ): 11.57 (1H, s), 6.89 (2H, s), 4.21 (2H, q, J=7.1 Hz), 2.35 (3H, s), 1.24 (3H, t, J=7.1 Hz)

Preparation 13

A solution of ethyl 2-(2-amino-5-methylthiazol-4-yl)-2-(Z)-(hydroxyimino)acetate (8.73 g) in dimethylformamide (60 ml) was treated portionwise with trityl chloride (11.7 g) and dropwise with triethylamine (6.4 ml). The reaction mixture was quenched by water and extracted with ethyl acetate. The combined extracts were washed with water and brine, and were dried with magnesium sulfate. The solvent was removed under reduced pressure to afford ethyl 2-(Z)-hydroxyimino-2-(5-methyl-2-tritylaminothiazol-4-yl) acetate (16.15 g).

IR (KBr): 1740, 1539, 1520, 702 cm$^{-1}$; NMR (DMSO-d$_6$, δ): 11.43 (1H, s), 8.44 (1H, s), 7.16–7.40 (15H, m), 3.74 (2H, q, J=7.1 Hz), 2.25 (3H, s), 1.05 (3H, t, J=7.1 Hz)

Preparation 14

To a suspension of sodium hydride (1.37 g) in 110 ml of ethyl acetate, ethyl 2-(5-methyl-2-tritylaminothiazol-4-yl)-2-(Z)-(hydroxyimino)acetate (16.15 g) was added at room temperature. The mixture was treated with a solution of trityl chloride (9.55 g) in ethyl acetate (66 ml). After 20 hours, the reaction was quenched by ice-water. The aqueous phase was extracted with ethyl acetate, and the combined extracts were washed with brine and dried with magnesium sulfate. The solvent was removed under reduced pressure, and the residue was purified by column chromatography on silica gel with 5%–17% ethyl acetate/hexane to give 9.8 g of ethyl 2-(5-methyl-2-tritylaminothiazol-4-yl)-2-(Z)-(trityloxyimino)acetate.

IR (KBr): 1740, 1540, 1515, 702 cm$^{-1}$; NMR (DMSO-d$_6$, δ): 8.51 (1H, s), 7.13–7.36 (30H, m), 3.93 (2H, q, J=7.1 Hz), 1.74 (3H, s), 1.13 (3H, t, J=7.1 Hz)

Preparation 15

A solution of ethyl 2-(5-methyl-2-tritylaminothiazol-4-yl)-2-(Z)-(trityloxyimino)acetate (9.8 g) in dioxane (40 ml) and water (40 ml) was treated with sodium hydroxide (2.75 g). The mixture was allowed to warm to 100° C. The reaction mixture was cooled to room temperature, diluted with water, and filtered to give a precipitate. A suspension of the precipitate in water and ethyl acetate was allowed to pH 2.5, the organic phase was washed with brine and dried with magnesium sulfate. The solvent was removed under reduced pressure to afford (5-methyl-2-tritylaminothiazol-4-yl)-2-(Z)-(trityloxyimino) acetic acid (9.55 g).

IR (KBr): 1738, 702 cm$^{-1}$; NMR (DMSO-d$_6$, δ): 8.47 (1H, s), 7.15–7.34 (30H, m), 1.68 (3H, s)

Preparation 16

To a solution of diphenylmethyl 7β-amino-3-[(1H-1,2,3-triazol-4-yl)thiomethylthio]-3-cephem-4-carboxylate (9.9 g) in formic acid (39.6 ml) was added conc. hydrochloric acid (8.54 ml) at room temperature, and the mixture was stirred at the same temperature for 2.5 hours. The mixture was poured into a mixture of acetone (297 ml) and ethyl acetate (594 ml) under ice-cooling, and the resulting precipitate was collected by filtration. The precipitate was resolved in water, and adjusted to pH 4 with 28% ammonium hydroxide under ice-cooling. The precipitate was collected by filtration to give 7β-amino-3-[(1H-1,2,3-triazol-4-yl) thiomethylthio]-3-cephem-4-carboxylic acid (5.42 g).

NMR (DMSO-d$_6$, δ): 3.78 (2H, br s), 4.38 (2H, m), 4.75 (1H, d, J=5.0 Hz), 4.97 (1H, d, J=5.0 Hz), 8.00 (1H, s)

EXAMPLE 1

Under nitrogen atmosphere, phosphorus oxychloride (0.52 ml) was added to a solution of N,N-dimethylformamide (0.44 ml) in ethyl acetate (2.5 ml) with ice-cooling. After 10 minutes stirring, the mixture was diluted with tetrahydrofurane (25 ml) and then 2-(5-chloro-2-formylaminothiazol-4-yl)-2-(Z)-(2cyclopenten-1-yloxyimino) acetic acid (1.36 g) was added to the mixture. The mixture was stirred for 1 hour at the same temperature (Solution A).

Bis(trimethylsilyl)acetamide (5.9 ml) was added to a solution of diphenylmethyl 7β-amino-3-[(1-tritylpyrazol-4-yl)methylthio]- 3-cephem-4-carboxylate (2.88 g) in N,N-dimethylacetamide (30 ml) with ice-cooling (Solution B).

Solution A was added slowly to the solution B under stirring for 30 minutes. The whole mixture was stirred for 1 hour at 0° C., then poured into the mixture of water and ethyl acetate while the reaction pH was adjusted between 6.0 and 7.0 with 10% aqueous potassium carbonate. The organic layer was collected, washed with water and brine and dried over magnesium sulfate.

After evaporation of the solvent, the residue was purified on silica gel (eluent: dichloromethaneacetone) to afford diphenylmethyl 7 β-[2-(5-chloro-2-formylaminothiazol-4-yl)-2-(Z)-(2-cyclopenten-1-yloxyimino)acetamido]-3-3-[(1-tritylpyrazol-4-yl)methylthio]-3-cephem-4-carboxylate (3.82 g).

IR (KBr): 1785.8, 1689.3 cm$^{-1}$;

NMR (DMSO-d$_6$, δ): 1.80–2.30 (4H, m), 3.81 (2H, s), 4.03 (2H, s), 5.14 (1H, d, J=4.68 Hz), 5.34 (1H, s), 5.80–5.95 (2H, m), 6.13 (1H, d, J=5.64 Hz), 6.84 (1H, s)

EXAMPLE 2

To a stirred mixture of solution of diphenylmethyl 7β-[2-(5-chloro-2-formylaminothiazol-4-yl)-2-(Z)-(2-cyclopenten-1-yloxyimino)acetamido]-3-[(1-tritylpyrazol-4-yl)methylthio]-3-cephem-4-carboxylate (3.82 g) in the mixture of methanol (40 ml) and tetrahydrofurane (12 ml) was added dropwise conc. hydrochloric acid (i.56 ml) at room temperature. After the mixture was stirred for 3 hours, the solvent was evaporated in vacuo. The residue was diluted with the mixture of water and ethyl acetate while the pH was adjusted between 8.0 and 8.5 with saturated sodium hydrogen carbonate. The organic layer was collected, washed with water and brine and dried over magnesium sulfate. After evaporation of the solvent, the residue was purified on silica gel (eluent: dichloromethane-acetone) to afford diphenylmethyl 7β-[2-(2-amino-5-chlorothiazol-4-yl)-2-(Z)-(2-cyclopenten-1-yloxyimino)acetamido]-3-[(pyrazol-4-yl)methylthio]-3-cephem-4-carboxylate (1.77 g).

IR (KBr): 3320.8, 1780.0, 1679.7, 1614.1 cm$^{-1}$; NMR (DMSO-d$_6$, δ): 1.80–2.30 (4H, m), 3.86 (2H, s), 4.05 (2H, s), 5.18 (1H, d, J=4.66 Hz), 5.29 (1H, s), 5.79 (1H, dd, J=8.62, 4.72 Hz), 5.91 (1H, s), 6.10 (1H, s), 6.83 (1H, s), 7.20–7.65 (14H, m), 9.55 (1H, d, J=8.40 Hz), 12.76 (1H, s)

EXAMPLE 3

Under nitrogen atmosphere, trifluoroacetic acid (4.0 ml) was added dropwise to a solution of diphenylmethyl 7β-[2-(2-amino-5-chlorothiazol-4-yl)-2-(Z)-(2-cyclopenten-1-yloxyimino)acetamido]-3-[(pyrazol-4-yl)methylthio]-3-cephem-4-carboxylate (1.71 g) in the mixture of dichloromethane (6.0 ml) and anisole (2.0 ml) at 0° C. Stirring was continued for 2 hours at the same temperature, the mixture was poured into isopropyl ether (200 ml). The resulting precipitate was collected by filtration, and then dissolved in the mixture of ethyl acetate and pH 6.86 buffer. The organic layer was removed, and the aqueous layer was adjusted pH 3.0 with 1N hydrochloric acid, concentrated in vacuo, then chlomatographed on a HP-20 column (eluent: water-methanol) to afford 7β-[2-(2-amino-5-chlorothiazol-4-yl)-2-(Z)-(hydroxyimino)acetamido]-3-[(pyrazol-4-yl)methylthio]-3-cephem-4-carboxylic acid (418.3 mg).

IR (KBr): 3236.0, 1764.5, 1648.8, 1616.1 cm$^{-1}$; NMR (DMSO-d$_6$, δ): 3.75 (2H, s), 4.00 (2H, s), 5.11 (1H, d, J=4.72 Hz), 5.72 (1H, dd, J=8.64, 4.68 Hz), 7.29 (2H, s), 7.55 (2H, s), 9.39 (1H, d, J=8.66 Hz), 11.70 (1H, s)

EXAMPLE 4

Under nitrogen atmosphere, trimethylsilylacetamide (39.4 g) and trimethylchlorosilane (0.76 ml) were added successively to a suspension of 7β-amino-3-[(pyrazol-4-yl)methylthio]-3-cephem-4-carboxylic acid (9.4 g) in dichloromethane (100 ml) at 0° C. The mixture was refluxed for 1.5 hours, then cooled again to −15° C. with dry ice-acetate. 2-(5-Chloro-2-formylaminothiazol-4-yl)-2-(Z)-(acetoxyimino)acetyl chloride (12.6 g) was added portionwise to the mixture over 10 minutes at the same temperature. The whole mixture was stirred for 12 hours at 0° C., then poured into 100 ml of ice-cooled methanol. After the solvent was concentrated in vacuo, 17 ml of concentrated hydrogen chloride was added at 0° C., and stirred for 7 hours. The mixture was poured into water (400 ml) and the pH was adjusted to between 3.4 and 3.6 with 28% ammonium hydroxide, and stirred for 12 hours at 0° C. The resulting precipitate was collected by filtration, and chromatographed on HP-20 to afford 7β-[2-(2-amino-5-chlorothiazol-4-yl)-2-(Z)-(hydroxyimino)-acetamido]-3-[(pyrazol-4-yl)methylthio]-3-cephem-4-carboxylic acid (6.30 g) as crystals. The physical data was identical with that the object compound of Example 3.

Philip MPD 188 X-Ray

Powder Diffraction System

| 2θ | intensity |
| --- | --- |
| 7.0 | 0.13 |
| 7.2 | 0.12 |
| 12.0 | 0.27 |
| 13.0 | 0.09 |
| 18.0 | 0.10 |
| 18.5 | 0.35 |
| 19.5 | 0.22 |
| 20.5 | 0.22 |
| 21.5 | 0.20 |

-continued

| 2θ | intensity |
| --- | --- |
| 22.0 | 0.26 |
| 24.5 | 0.26 |
| 26.0 | 0.15 |
| 27.5 | 0.15 |

EXAMPLE 5

(1) Diphenylmethyl 7β-[2-(5-fluoro-2-formylaminothiazol-4-yl)-2-(Z)-(formyloxyimino)acetamido]-3-[(1-tritylpyrazol-4-yl)methylthio]-3-cephem-4-carboxylate was obtained from 2-(5-fluoro-2-formylaminothiazol-4-yl)-2-(Z)-(formyloxyimino)- acetic acid and diphenylmethyl 7β-amino- 3-[1-tritylpyrazol-4-yl)methylthio]-3-cephem-4-carboxylate according to a similar manner to that of Example 1.

NMR (DMSO-d$_6$, δ): 3.80 (2H, br s), 4.05 (2H, br s), 5.15 (1H, d, J=4.7 Hz), 5.87 (1H, dd, J=4.7 Hz, 8.67 Hz), 6.84 (1H, s), 7.00–7.55 (27H, m), 7.95 (1H, s), 8.48 (1H, s), 9.60 (1H, J=8.67 Hz), 11.89 (1H, s)

(2) Diphenylmethyl 7β-[2-(2-amino-5-bromothiazol-4-yl)-2-(Z)-(acetoxyimino)acetamido]-3-[(1-tritylpyrazol-4-yl)-methylthio]-3-cephem-4-carboxylate (4.55 g) was obtained from 2-(2-amino-5-bromothiazol-4-yl)-2-(Z)-(acetoxyimino)acetic acid (2.21 g) and diphenylmethyl 7β-amino-3-[(1-tritylprazoyl-4-yl)methylthio]-3-cephem-4-carboxylate (3.60 g) according to a similar manner to that of Example 1.

IR (KBr): 1780.0, 1695.1, 1614.1 cm$^{-1}$; NMR (DMSO-d$_6$, δ): 2.19 (3H, s), 3.83 (2H, s), 4.04 (2H, s), 5.19 (1H, d, J=4.66 Hz ), 5.83 (1H, dd, J=8.38, 4.62 Hz), 6.84 (H, s), 6.95–7.56 (29H, m), 9.90 (1H, d, J=8.44 Hz); MASS: 1012 (M$^+$+1)

EXAMPLE 6

The following compounds were obtained according to a similar manner to that of Example 2.

(1) Diphenylmethyl 7β-[2-(2-amino-5-fluorothiazol-4-yl)-2-(Z)-(hydroxyimino)acetamido]-3-[ (pyrazol-4-yl)-methylthio]-3-cephem-4-carboxylate NMR (DMSO-d$_6$, δ): 3.85 (2H, br s), 4.07 (2H, br s), 5.19 (1H, d, J=4.7 Hz), 5.80 (1H, dd, J=4.5 Hz, 8.67 Hz), 6.83 (1H, s), 7.10–7.23 (14H, m), 9.48 (1H, d, J=8.67 Hz), 11.55 (1H, s)

(2) Diphenylmethyl 7β- 2-(2-amino-5-bromothiazol-4-yl)-2-(Z)-(hydroxyimino)acetamido]-3-[(pyrazol-4-yl)-methylthio]-3-cephem-4-carboxylate IR (KBr): 3330.5, 1776.1, 1677.8, 1612.1 cm$^{-1}$; NMR (DMSO-d$_6$, δ): 3.85 (2H, s), 4.04 (2H, s), 5.19 (1H, d, J=4.68 Hz), 5.81 (1H, dd, J=8.72, 4.66 Hz), 6.83 (1H, s), 7.20–7.60 (14H, m), 9.43 (1H, d, J=8.72 Hz), 11.73 (1H, s); MASS: J=728 (M$^+$+1)

EXAMPLE 7

The following compounds were obtained according to a similar manner to that of Example 3.

(1) 7β-[2-(2-Amino-5-fluorothiazol-4-yl)-2-(Z)-(hydroxyimino)acetamido]-3-[(pyrazol-4-yl)methylthio]-3-cephem-4-carboxylic acid IR (KBr): 1766, 1673, 1621, 1535, 1390, 1218 cm$^{-1}$; NMR (DMSO-d$_6$, δ): 3.74 (2H, br s), 4.05 and 3.97 (2H, ABq, J=13.4 Hz), 5.11 (1H, d, J=4.7 Hz), 5.16 (1H, dd, J=4.7 Hz, 8.67 Hz), 7.00 (2H, br s), 7.55 (2H, s), 9.41 (1H, d, J=8.67 Hz), 11.50 (1H, s); FAB MASS: 500 (M$^+$)

(2) 7β-[2-(2-Amino-5-bromothiazol-4-yl)-2-(Z)-(hydroxyimino)acetamido]-3-[(pyrazol-4-yl)methylthio]-3-cephem-4-carboxylic acid IR (KBr): 3236.0, 1766.5, 1648.8 cm$^{-1}$; NMR (DMSO-d$_6$, δ): 3.75 (2H, s), 4.00 (2H, s), 5.11 (1H, d, J=4.72 Hz), 5.71 (1H, dd, J=8.60, 4.64 Hz), 7.31 (2H, s), 7.54 (2H, m, 9.36 (1H1 d, J=8.60 Hz), 11.70 (2H, s); MASS: 558 (M$^+$)

(3) 7β-[2-(2-Amino-5-methylthiazol-4-yl)-2-(Z)-(hydroxyimino)acetamido]-3-[(pyrazol-4-yl)methylthio]-3-cephem-4-carboxylic acid IR (KBr): 1765, 1668, 1610, 1535, 1392, 1354 cm$^{-1}$; NMR (DMSO-d$_6$, δ): 2.33 (3H, s), 3.75 (2H, s), 3.90–4.10 (2H, m), 5.10 (1H, d, J=4.7 Hz), 5.72 (1H, dd, J=4.7 Hz, 8.7 Hz), 6.83 (2H, s), 7.55 (2H, s), 9.27 (1H, d, J=8.7 Hz), 11.29 (1H, s); FAB MASS (m/z): 495 (M$^+$)

EXAMPLE 8

Phosphorus oxychloride (0.42 g) was added to an ice-cooled solution of ethyl acetate (2 ml) and N,N-dimethylformamide (0.21 ml), and then stirred for 30 minutes at 5° C. Ethyl acetate (5.0 ml) and 2-[5-methyl-2-tritylaminothiazol-4-yl]-2-(Z)-(trityloxyimino)acetic acid (1.7 g) was added thereto at 5° C., the reaction mixture was stirred for 30 minutes at the same temperature. [Solution (A)]

On the other hand, N,O-bis(trimethylsilyl)acetamide (2.72 g) was added to an ice-cooled solution of diphenylmethyl 7β-amino-3-[(1-tritylpyrazol-4-yl)methylthio]-3-cephem-4-carboxylate (1.61 g) in N,N-dimethylacetamide (16 ml), and then stirred for one hour at 5° C. After that, the above Solution (A) was poured into this solution. After the reaction mixture was stirred for 2 hours at 50° C., the mixture was poured into ethyl acetate (100 ml) and water (100 ml), adjusted to pH 6.5 with 1N potassium hydroxide. The organic layer was separated, dried over magnesium sulfate, and evaporated. The residue was suspended into methanol (20 ml). Concentrated hydrochloric acid (0.51 ml) was added thereto at room temperature. The reaction mixture was stirred for 4 hours at 25° C., then it was poured into ethyl acetate (80 ml) and water (70 ml). The mixture was adjusted to pH 6.5 with 2N aqueous potassium hydroxide. The organic layer was separated, dried over magnesium sulfate and evaporated. The resulting precipitate was collected and washed with diisopropyl ether (10 ml) to give diphenylmethyl 7β-[2-(2-amino-5-methylthiazol-4-yl)-2-(Z)-(hydroxyimino)acetamido]-3-[(pyrazol-4-yl)methylthio]-3-cephem-4-carboxylate (0.61 g)

IR (KBr): 1782, 1761, 1686, 1674, 1605 cm$^{-1}$; NMR (DMSO-d$_6$, δ): 1.84 (3H, s), 3.86 (2H, s), 3.98, 4.10 (2H, ABq, J=16 Hz), 5.30 (1H, d, J=4.7 Hz), 6.02 (1H, dd, J=4.7 Hz, 9.0 Hz), 6.86 (1H, s), 7.20–7.60 (14H, m), 9.70 (1H, d, J=9.0 Hz); FAB MASS (m/z): 662 (M$^+$+1)

EXAMPLE 9

The following compounds were obtained according to a similar manner to that of Example 4.

(1) 7β-[2-(2-Amino-5-chlorothiazol-4-yl)-2-(Z)-(hydroxyimino)acetamido]-3-(4-pyridylmethylthio)-3-cephem-4-carboxylic acid IR (KBr): 1766.5, 1660.4 cm$^{-1}$; NMR (DMSO-d$_6$, δ): 3.68 (2H, s), 4.12 (2H, s), 5.10 (1H, d, J=4.8 Hz), 5.73 (1H, dd, J=8.6 Hz, 4.8 Hz), 7.28 (2H, br s), 7.34 (2H, d, J=5.9 Hz), 8.51 (2H, d, J=5.9 Hz), 9.38 (1H, d, J=8.6 Hz), 11.69 (1H, s)

(2) 7β-[2-(2-Amino-5-chlorothiazol-4-yl)-2-(Z)-(hydroxyimino)acetamido]-3-[(Z)-2-(3-pyridyl)vinylthio]-3-cephem-4-carboxylic acid IR (KBr): 1783.8, 1766.5, 1673.9, 1637.3, 1612.2 cm$^{-1}$; NMR (DMSO-d$_6$, δ): 3.68 and 4.04 (2H, ABq), J=17.5 Hz), 5.19 (1H, d, J=4.9 Hz), 5.82 (1H, d, J=8.5 Hz, 4.9 Hz), 6.74 (1H, d, J=10.8 Hz), 6.81 (H, d, J10.8 Hz), 7.28 (2H, br m), 7.42–7.48 (1H, m), 7.84–7.90 (1H, m), 8.45–8.47 (1H, m), 8.64–8.65 (1H, m), 9.44 (1H, d, J=8.5 Hz), 11.71 (1H, s)

(3) 7β-[2-(2-Amino-5-chlorothiazol-4-yl)-2-(Z)-(hydroxyimino)acetamido]-3-[(Z)-3-(carbamoyloxy)-1-5 propenyl]-3-cephem-4-carboxylic acid IR (KBr): 1772.3, 1710.6, 1664.3, 1604.5 cm$^{-1}$; NMR (DMSO-d$_6$, δ): 3.47 and 3.63 (2H, ABq, J=17.7 Hz), 4.42–4.49 (2H, m), 5.18 (1H, d, J=4.9 Hz), 5.55–5.67 (1H, m), 5.79 (1H, dd, J=8.6 Hz, 4.9 Hz), 6.31 (1H, d, J=11.7 Hz), 6.52 (2H, br s), 7.29 (2H, br s), 9.40 (1H, d, J=8.6 Hz), 11.69 (1H, s)

(4) 7β-[2-(2-Amino-5-chlorothiazol-4-yl)-2-(Z)-(hydroxyimino)acetamido]-3-(N,N-dimethylcarbamoyloxymethyl)-3-cephem-4-carboxylic acid IR (KBr): 1774.2, 1691.3, 1662.3, 1631.5 cm$^{-1}$; NMR (DMSO-d$_6$, δ): 2.83 (6H, s), 3.46 and 3.60 (2H, ABq, J=18.2 Hz), 4.64 and 4.98 (2H, ABq, J=18.2 Hz), 5.12 (1H, d, J=4.9 Hz), 5.79 (1H, dd, J=8.6 Hz, 4.9 Hz), 7.28 (2H, br s), 9.38 (1H, d, J=8.6 Hz), 11.69 (1H, s)

(5) 7β-[2-(2-Amino-5-chlorothiazol-4-yl)-2-(Z)-(hydroxyimino)acetamido]-3-[(1H-1,2,3-triazol-4-yl)-thiomethylthio]-3-cephem-4-carboxylic acid IR (KBr): 1766.5, 1670.1, 1614.1 cm$^{-1}$; NMR (DMSO-d$_6$, δ): 3.80 (2H, br s), 4.41 (2H, br s), 5.13 (1H, d, J=4.8 Hz), 5.76 (1H, dd, J=8.7 Hz, 4.8 Hz), 7.28 (2H, br s), 9.40 (1H, d, J=8.7 Hz), 11.70 (1H, s)

(6) 7β-[2-(2-Amino-5-chlorothiazol-4-yl)-2-(Z)-(hydroxyimino)acetamido]-3-[(Z)-2-(3-pyridyl)vinyl]-3-cephem-4-carboxylic acid IR (KBr): 1770.3, 1670.1, 1616.1 cm$^{-1}$; NMR (DMSO-d$_6$, δ): 3.16 and 3.54 (2H, ABq, J=17.9 Hz), 5.21 (1H, d, J=4.9 Hz), 5.81 (1H, dd, J=8.6 Hz, 4.9 Hz), 6.53 (1H, d, J=12.2 Hz), 6.60 (1H, d, J=12.2 Hz), 7.27 (2H, br s), 7.28–7.38 (1H, m), 7.63–7.67 (1H, m), 8.43–8.46 (2H, m), 9.44 (1H, d, J=8.6 Hz), 11.67 (1H, s)

(7) 7β-[2-(2-Amino-5-chlorothiazol-4-yl)-2-(Z)-(hydroxyimino)acetamido]-3-cephem-4-carboxylic acid IR (KBr): 3326.6, 1781.9, 1658.5 cm$^{-1}$; NMR (DMSO-d$_6$, δ): 3.40–3.65 (2H, m), 5.06 (1H, d, J=5.0 Hz), 5.81 (1H, dd, J=8.56 Hz, 5.16 Hz), 6.40–6.49 (1H, m), 7.29 (2H, m), 9.38 (1H, d, J=8.62 Hz), 11.69 (1H, m); FAB-MASS (m/z): 403.6 (M$^+$)

EXAMPLE 10

To a solution of 7β-amino-3-vinyl-3-cephem-4-carboxylic acid (1 g) and N-(trimethylsilyl)acetamide (5.8 g) in dichloromethane (10 ml) was added 2-(2-amino-5-chlorothiazol-4-yl)-2-(Z)-(acetoxyimino) acetyl chloride (1.69 g) under ice-cooling. After being stirred at the same temperature for 1 hour, to this mixture was added methanol (10 ml). After evaporating in vacuo to remove the dichloromethane, the residue was added conc. hydrochloric acid (1.95 ml) at room temperature. After being stirred at the same temperature for 4 hours, the mixture was poured into water (10 ml). The mixture was adjusted to pH 3.5 with 28% ammonium hydroxide in water, and the resulting precipitate was collected by filtration to afford 7β-[2-(2-amino-5-chlorothiazol-4-yl)-2-(Z)-(hydroxyimino)acetamido]-3-vinyl-3-cephem-4-carboxylic acid (137 mg).

IR (KBr): 1770.3, 1670.1, 1621.8 cm$^{-1}$; NMR (DMSO-d$_6$, δ): 3.52 and 3.72 (2H, ABq, J=17.8 Hz), 5.16 (1H, d, J=4.9 Hz), 5.29 (1H, d, J=11.4 Hz), 5.57 (1H, d, J=17.4 Hz), 5.79 (1H, dd, J=8.6 Hz, 4.9 Hz), 6.90 (1H, dd, J=17.4 Hz, 11.4 Hz), 7.29 (2H, br s), 9.42 (1H, d, J=8.6 Hz), 11.71 (1H, s)

We claim:

1. A compound of the formula:

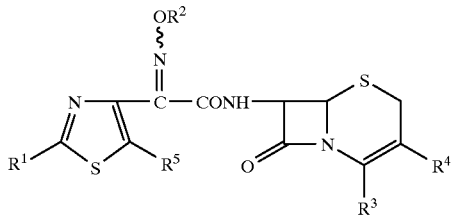

wherein $R^1$ is amino, $R^2$ is hydrogen, $R^3$ is carboxy, $R^4$ is heterocyclic(lower)alkylthio wherein said heterocyclic group is pyrazolyl and said lower alkyl group is methyl, and $R^5$ is halogen; and pharmaceutically acceptable salts thereof.

2. A compound of claim 1, which is 7 β-[2-(2-amino-5-chlorothiazol-4-yl)-2-(z)-(hydroxyimino)acetamido]-3-[(pyrazol-4-yl)methylthio]-3-cephem-4-carboxylic acid and its pharmaceutically acceptable salts.

3. A method for the treatment of bacterial infectious diseases which comprises administering a compound of claim 1 or a pharmaceutically acceptable salt thereof to human or animals.

4. A process for preparing a compound of the formula:

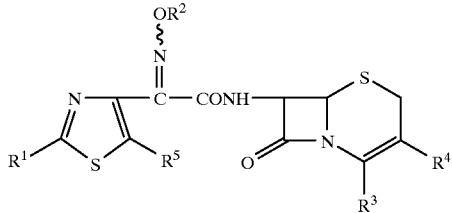

wherein $R^1$ is amino, $R^2$ is hydrogen, $R^3$ is carboxy, $R^4$ is heterocyclic(lower)alkylthio wherein said heterocyclic group is pyrazolyl and said lower alkyl group is methyl, and $R^5$ is halogen; or salts thereof, which comprises (1) reacting a compound of the formula:

(II)

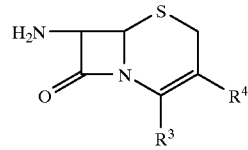

wherein $R^3$ and $R^4$ are each as defined above, or its reactive derivative at the amino group, or a salt thereof with a compound of formula

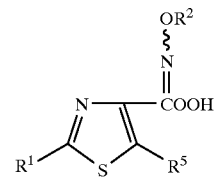

wherein $R^1$, $R^2$ and $R^5$ are each as defined above, or its reactive derivative at the carboxy group, or a salt thereof, to give a compound of the formula:

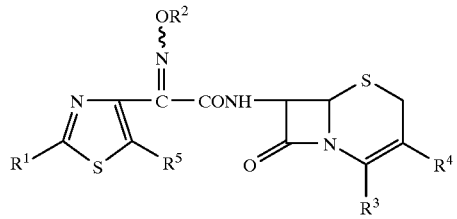

wherein $R^1$, $R^2$, $R^3$, $R^4$ and $R^5$ are each as defined above, or a salt thereof, or (2) subjecting a compound of the formula:

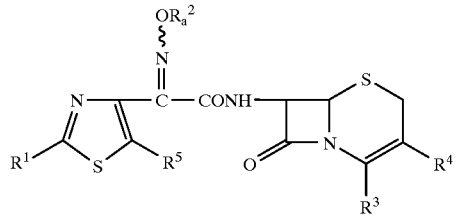

wherein $R^1$, $R^3$, $R^4$ and $R^5$ are each as defined above, and $R_a^2$ is hydroxy protective group, or a salt thereof, to an elimination reaction of the hydroxy protective group, to give a compound of the formula:

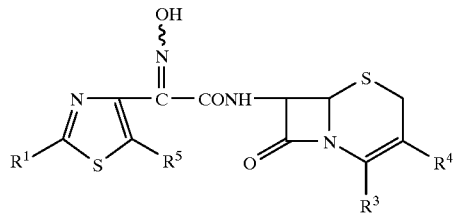

wherein $R^1$, $R^3$, $R^4$ and $R^5$ are each as defined above, or a salt thereof, or (3) subjecting a compound of the formula:

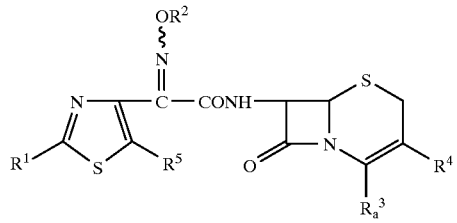

wherein $R^1$, $R^2$, $R^4$ and $R^5$ are each as defined above, $R_a^3$ is protected carboxy or a salt thereof, to an elimination reaction of the carboxy protective group to give a compound of formula:

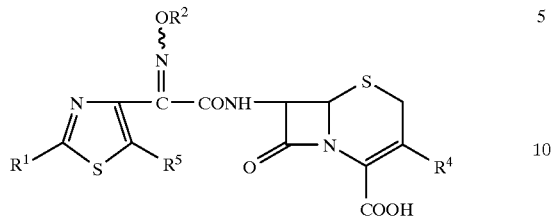

wherein $R^1$, $R^2$, $R^4$ and $R^5$ are each as defined above, or a salt thereof, or (4) subjecting a compound of formula:

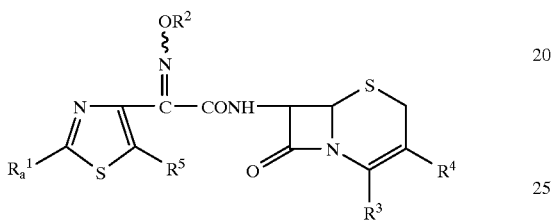

wherein, $R^2$, $R^3$, $R^4$ and $R^5$ are each as defined above, and
$R_a^1$ is protected amino,
or a salt thereof, to an elimination reaction of the amino protective group, to give a compound of the formula:

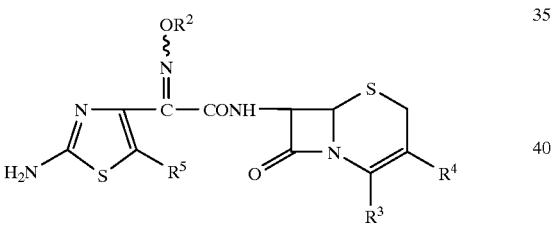

wherein, $R^2$, $R^3$, $R^4$ and $R^5$ are each as defined above, or a salt thereof, (5) subjecting a compound of the formula:

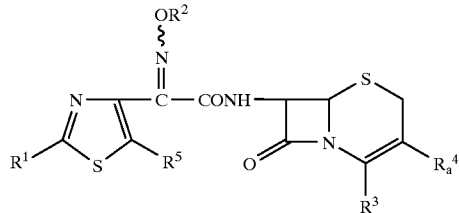

wherein $R^1$, $R^2$, $R^3$ and $R^5$ are each as defined above,
$R_a^4$ is substituted heterocyclic(lower)alkylthio wherein said heterocyclic group is pyrazolyl and said lower alkyl group is methyl, which is substituted by imino protective group, or a salt thereof, to an elimination reaction of imino protective group, to give a compound of the formula:

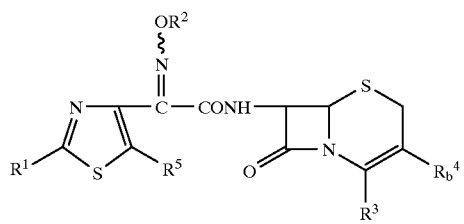

wherein $R^1$, $R^2$, $R^3$, and $R^5$ are each as defined above, and $R_a^4$ is heterocyclic(lower)alkylthio wherein said heterocyclic group is pyrazolyl and said lower alkyl group is methyl, or a salt thereof.

5. A pharmaceutical composition which comprises, as an active ingredient, a compound of claim 1 or a pharmaceutically acceptable salt thereof in admixture with pharmaceutically acceptable carriers.

* * * * *